(12) United States Patent
Cheng et al.

(10) Patent No.: US 7,820,844 B2
(45) Date of Patent: Oct. 26, 2010

(54) CONJUGATED COMPOUNDS CONTAINING HETEROATOM-CENTER-ARYLSILANE DERIVATIVES AND THEIR APPLICATION

(75) Inventors: Chien-Hong Cheng, No. 101, Section 2 Kuang Fu Rd., Department of Chemistry, Tsing Hua University, Hsinchu (TW) 30013; Hung-Hsin Shih, Hsinchu (TW); Ho-Hsiu Chou, Hsinchu (TW)

(73) Assignee: Chien-Hong Cheng, Hsinchu (TW)

( * ) Notice: Subject to any disclaimer, the term of this patent is extended or adjusted under 35 U.S.C. 154(b) by 107 days.

(21) Appl. No.: 11/876,568

(22) Filed: Oct. 22, 2007

(65) Prior Publication Data

US 2009/0105487 A1    Apr. 23, 2009

(51) Int. Cl.
   *C07F 7/02*    (2006.01)
(52) U.S. Cl. .................. 556/412; 556/413; 556/402
(58) Field of Classification Search ................ 556/412, 556/413, 402
   See application file for complete search history.

(56) References Cited

U.S. PATENT DOCUMENTS 5,187,310 A * 2/1993 Mishima et al. ............. 556/413

OTHER PUBLICATIONS

Bai et al. publication, Chem. Eur. J, May 16, 2007, 13:5713-5723.*
Kurimoto et al., 1998, CAS: 129:296147.*

* cited by examiner

*Primary Examiner*—Rei-tsang Shiao
(74) *Attorney, Agent, or Firm*—WPAT, PC; Justin King

(57) ABSTRACT

The present invention discloses conjugated compounds containing heteroatom-centered arylsilane derivatives and their applications as host materials, electron transport materials, or hole transport materials in an organic electroluminescent device. The general structure of the conjugated compounds containing heteroatom-centered arylsilane derivatives is as follows:

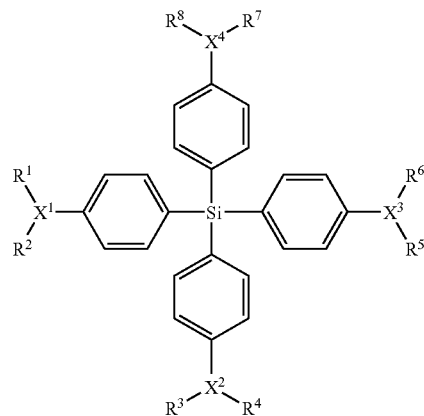

where $X^1$, $X^2$, $X^3$, and $X^4$ can be identical or different and $X^1$, $X^2$, $X^3$, and $X^4$ are independently selected from the group consisting of the following: H, B, N, P=O, Si—$R^9$; and $R^1$, $R^2$, $R^3$, $R^4$, $R^5$, $R^6$, $R^7$, $R^8$, and $R^9$ can be identical or different and $R^1$, $R^2$, $R^3$, $R^4$, $R^5$, $R^6$, $R^7$, $R^8$, and $R^9$ are independently selected from aryl group or heterocyclic aryl group containing one or more substituents.

8 Claims, No Drawings

CONJUGATED COMPOUNDS CONTAINING HETEROATOM-CENTER-ARYLSILANE DERIVATIVES AND THEIR APPLICATION

BACKGROUND OF THE INVENTION

1. Field of the Invention

The present invention is generally related to an aromatic conjugated compound, and more particularly to a conjugated compound containing heteroatom-centered arylsilane derivatives and its application in an organic electron device.

2. Description of the Prior Art

At present, phosphorescent metal complexes have been used as phosphorescent dopants in an organic light emitting diode. Among these metal complexes used in the light-emitting layer of the organic light emitting diode, cyclometalated iridium complexes have been extensively researched since their electron configurations have strong spin-orbit coupling. Since spin-orbit coupling results in mixing between the singlet and triplet excited states, the lifetime of the triplet state is greatly reduced and thereby the phosphorescence efficiency is promoted. In addition, it is found that the doping method can also enhance the efficiency of the device. Therefore, the method of doping phosphorescent substance in a host material is utilized and thus the research in blue phosphorescent host materials becomes important. In the earlier reports, the majority of the blue phosphorescent host materials are carbazoles. Carbazole derivatives have high triplet-state energy and are suitable as the blue phosphorescent host materials. In view of the above matter, developing a novel organic compound having high heat stability and high triplet-state energy to prolong the usage lifetime of the device and to increase luminance efficiency is still an important task for the industry.

SUMMARY OF THE INVENTION

In light of the above background, in order to fulfill the requirements of the industry, the present invention provides a novel compound containing heteroatom-centered arylsilane derivatives and its application as a host material, an electron transport material, or a hole transport material in an organic electronic device or its application as a hole and an electron transport material in a solar cell.

One object of the present invention is to provide a compound containing heteroatom-centered arylsilane derivatives having high heat stability to increase the usage lifetime of an organic electroluminescence device as well as the whole luminance efficiency of the device.

Another object of the present invention is to provide a compound containing heteroatom-centered arylsilane derivatives having high triplet-state energy difference, which can not be provided by the common blue phosphorescence host materials, and can be used together with various common phosphorescent materials, such as blue, green, and red phosphorescent materials, like iridium (Ir), platinum (Pt), and osmium (Os) metal complexes. Therefore, this present invention does have the economic advantages for industrial applications.

Accordingly, the present invention discloses a compound containing heteroatom-centered arylsilane derivatives and its applications as a host material, an electron transport material, or a hole transport materials in an organic electroluminescent device. The general structure of the compound containing heteroatom-centered arylsilane derivatives is as follows:

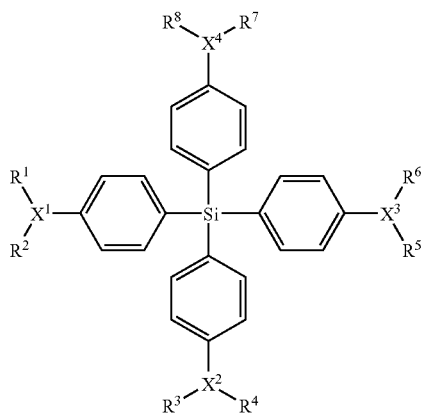

where $X^1$, $X^2$, $X^3$, and $X^4$ can be identical or different and $X^1$, $X^2$, $X^3$, and $X^4$ are independently selected from the group consisting of the following: H, B, N, P=O, Si—$R^9$; and $R^1$, $R^2$, $R^3$, $R^4$, $R^5$, $R^6$, $R^7$, $R^8$, and $R^9$ can be identical or different and $R^1$, $R^2$, $R^3$, $R^4$, $R^5$, $R^6$, $R^7$, $R^8$, and $R^9$ are independently selected from aryl group or heterocyclic aryl group containing one or more substituents.

The aryl group comprises phenyl, naphthyl, diphenyl, anthryl, pyrenyl, phenanthryl, fluorene, or other multi-phenyl group.

The heterocyclic aryl group comprises pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, phenanthroline, or other heterocyclic aryl group.

In addition, $R^1$, $R^2$, $R^3$, $R^4$, $R^5$, $R^6$, $R^7$, $R^8$, and $R^9$ groups each can have different number of the following substituent(s) or atom(s) at different position(s): H atom, halogen atom (such as fluorine, chlorine, bromine, iodine), aryl group, halogen substituted aryl group, C1-C20 haloalkyl substituted aryl group, C1-C20 haloalkyl substituted aralkyl group, aryl substituted C1-C20 alkyl group, C1-C20 alkyl group (such as methyl, ethyl, butyl, cyclohexyl), C1-C20 alkoxy group, amino group, C1-C20 substituted amino group, nitrile group, nitro group, carbonyl group, cyano group (—CN), and heterocyclic group.

The invention also discloses the application of the compound containing heteroatom-centered arylsilane derivatives, especially the application as a host material, an electron transport material, a hole transport material, and a light-emitting host material in an organic electroluminescence device or phosphorescence device; or the application as an electron transport material and a hole transport material in other organic electronic devices.

DESCRIPTION OF THE PREFERRED EMBODIMENTS

What is probed into the invention is a compound containing heteroatom-centered arylsilane derivatives. Detail descriptions of the processes and composition structures will be provided in the following in order to make the invention thoroughly understood. Obviously, the application of the invention is not confined to specific details familiar to those who are skilled in the art. On the other hand, the common processes and composition structures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, a compound containing heteroatom-centered arylsilane derivatives is disclosed. The general structure of the compound containing heteroatom-centered arylsilane derivatives is as follows:

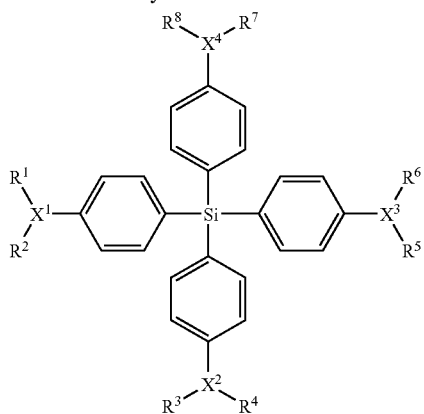

where $X^1$, $X^2$, $X^3$, and $X^4$ can be identical or different and $X^1$, $X^2$, $X^3$, and $X^4$ are independently selected from the group consisting of the following: H, B, N, P=O, Si—$R^9$; and $R^1$, $R^2$, $R^3$, $R^4$, $R^5$, $R^6$, $R^7$, $R^8$, and $R^9$ can be identical or different and $R^1$, $R^2$, $R^3$, $R^4$, $R^5$, $R^6$, $R^7$, $R^8$, and $R^9$ are independently selected from aryl group or heterocyclic aryl group containing one or more substituents.

At least one of the $X^1$, $X^2$, $X^3$, and $X^4$ is not H. When $X^1$ is H, $R^1$ and $R^2$ do not exist in the structure. When $X^2$ is H, $R^3$ and $R^4$ do not exist in the structure. When $X^3$ is H, $R^5$ and $R^6$ do not exist in the structure. When $X^4$ is H, $R^7$ and $R^8$ do not exist in the structure. Besides, according to this embodiment, when $X^1$ is N, $X^3$ is not N.

The aryl group comprises phenyl, naphthyl, diphenyl, anthryl, pyrenyl, phenanthryl, fluorene, or other multi-phenyl group.

The heterocyclic aryl group comprises pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, phenanthroline, or other heterocyclic aryl group.

In addition, $R^1$, $R^2$, $R^3$, $R^4$, $R^5$, $R^6$, $R^7$, $R^8$, and $R^9$ groups each can have one or more substituents. The substituent is independently selected from the group consisting of the following: H atom, halogen atom (such as fluorine, chlorine, bromine, iodine), aryl group, halogen substituted aryl group, C1-C20 haloalkyl substituted aryl group, C1-C20 haloalkyl substituted aralkyl group, aryl substituted C1-C20 alkyl group, C1-C20 alkyl group (such as methyl, ethyl, butyl, cyclohexyl), C1-C20 alkoxy group, amino group, C1-C20 substituted amino group, nitrile group, nitro group, carbonyl group, cyano group (—CN), and heterocyclic group. The above mentioned aryl group comprises phenyl, naphthyl, diphenyl, anthryl, pyrenyl, phenanthryl, fluorene, or other multi-phenyl group.

The heterocyclic group comprises pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, phenanthroline, or other heterocyclic aryl group.

The preferred examples of the structure and fabricating method for the compound containing heteroatom-centered arylsilane derivatives according to the invention are described in the following. However, the scope of the invention should be based on the claims, but is not restricted by the following examples.

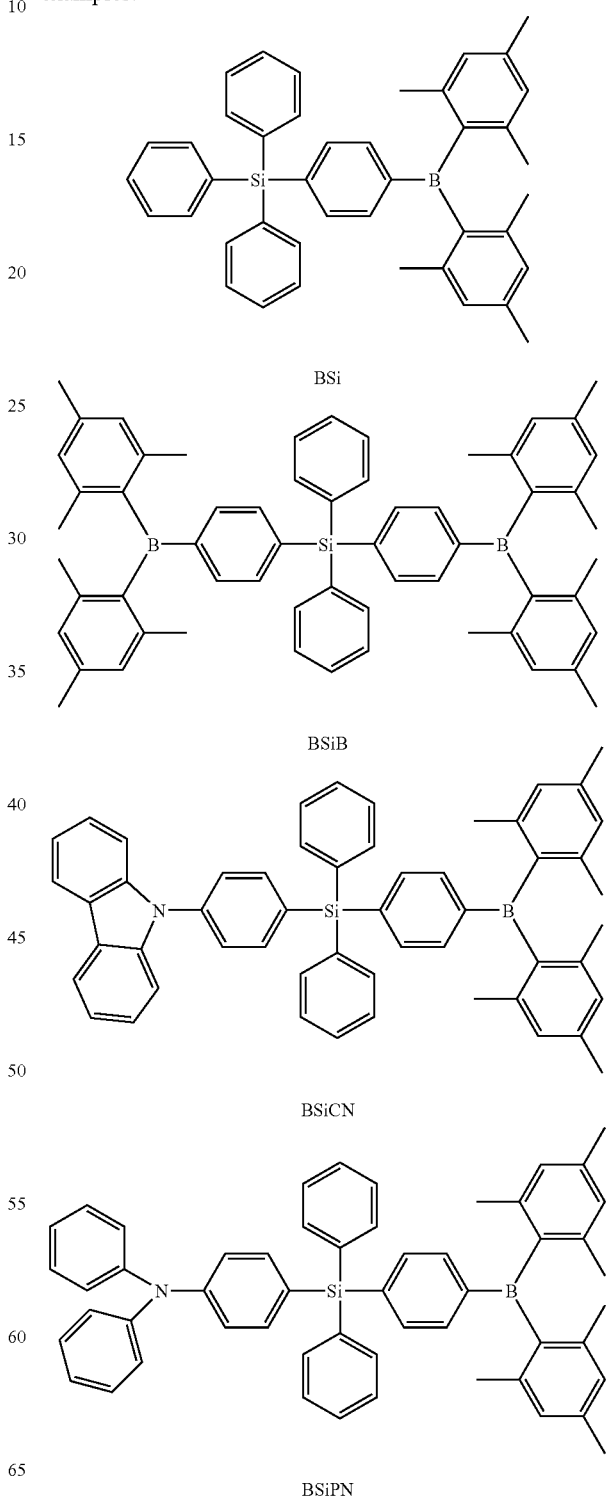

BSi

BSiB

BSiCN

BSiPN

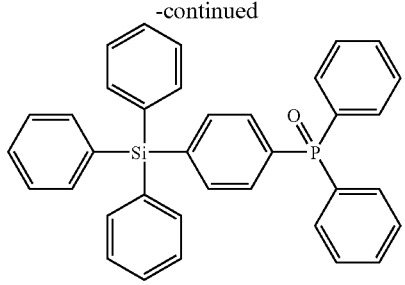

POSi

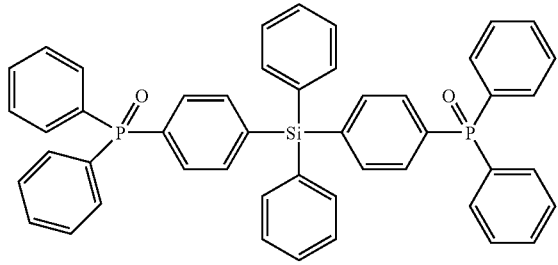

POSiPO

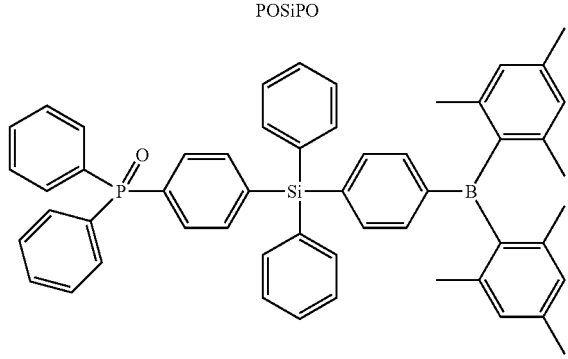

POSiB

Example 1

[4-(1,1-Dimseityboryl)phenyl](triphenyl)silane (hereinafter abbreviated as BSi

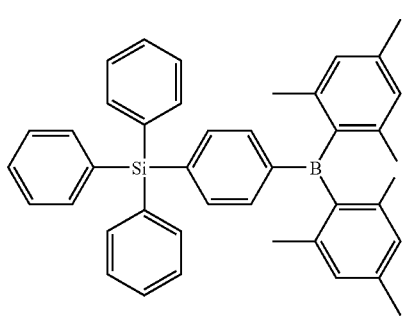

(4-Bromo-phenyl)-triphenyl-silane (2 mmole, 0.831 g) is placed in a 100 mL one-neck round-bottom flask. The flask is closed off with a cap and a suction needle is inserted through the cap to perform nitrogen injection and suction three times. Under the environment of filling with nitrogen, tetrahydrofuran (THF) 30 mL is added and then the temperature of the solution is dropped to −78° C. Then, n-BuLi (2.1 mmole, 0.9 mL, 2.5M) is injected and at −78° C. the solution is stirred for 40 minutes to form a lithium reagent. Separately, another 100 mL round-bottom flask is used to load a 10 mL of the solution formed by using THF to dissolve dimesitylboron fluoride (2.0 mmole, 0.595 g). A double-head needle is used to inject the latter solution into the lithium reagent. It is then stirred until the temperature of the solution becomes room temperature. After that, at room temperature the suction needle is removed and the reaction system is heated to 50° C. and maintained for 2 hrs. After the reaction is finished, proper amount of water and HCl is added. Extraction by methylene chloride and water is carried out. Magnesium sulfate is used to eliminate water. Then, the added magnesium sulfate is eliminated by filtration. After solvent is removed by suction, yellow-white solids are obtained. The yellow-white solids are washed by n-hexane and ether and after filtration white solids are collected, that is the compound BSi. The product yield is 70%.

$^1$H NMR (400 MHz, CDCl$_3$): δ: 7.54-7.52 (m, 8H), 7.46-7.39 (m, 5H), 7.36-7.32 (m, 6H), 6.78 (s, 4H), 2.27 (s, 6H), 1.99 (s, 12H). $^{13}$C NMR (100 MHz, CDCl$_3$): δ: 141.83, 140.79, 138.70, 138.58, 136.40, 135.88, 134.99, 134.29, 134.11, 129.62, 128.18, 127.88, 23.41, 21.18. HRMS (EI$^+$): Calcd for (C$_{42}$H$_{41}$BSi): 584.3071; found (M$^+$) 584.3065.

Example 2

Di[4-(1,1-dimseityboryl)phenyl](diphenyl)silane (hereinafter abbreviated as BSiB)

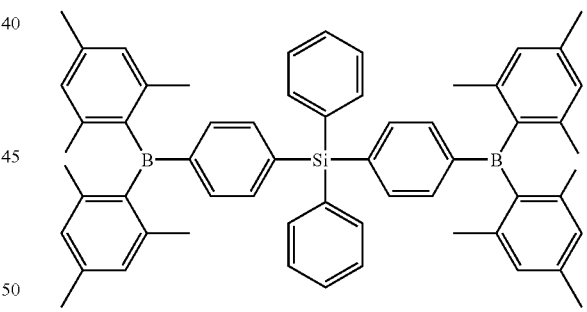

The synthetic method is the same as that in Example 1 except that bis-(4-bromo-phenyl)-diphenyl-silane is used instead of (4-bromo-phenyl)-triphenyl-silane. The two starting substances, dimetsitylboron fluoride and bis-(4-bromo-phenyl)-diphenyl-silane, have a equivalent ratio of 2:1. The product yield of BSiB is 65%.

$^1$H NMR (400 MHz, CDCl$_3$): δ: 7.53-7.50 (m, 8H), 7.45-7.38 (m, 6H), 7.35-7.32 (m, 4H), 6.78 (s, 8H), 2.27 (s, 12H), 1.99 (s, 24H). $^{13}$C NMR (100 MHz, CDCl$_3$): δ: 147.18, 141.77, 140.78, 138.70, 138.34, 136.35, 135.86, 134.99, 133.88, 129.66, 128.17, 127.88, 23.41, 21.19. HRMS (FAB$^+$): Calcd for (C$_{60}$H$_{62}$B$_2$Si): 832.48.07. found: (MH$^+$) 833.4882.

Example 3

9-(4-{1-[4-(1,1-dimseityboryl)phenyl]-1,1-diphenylsilyl}phenyl)-9H-carbazole (hereinafter abbreviated as BSiCN)

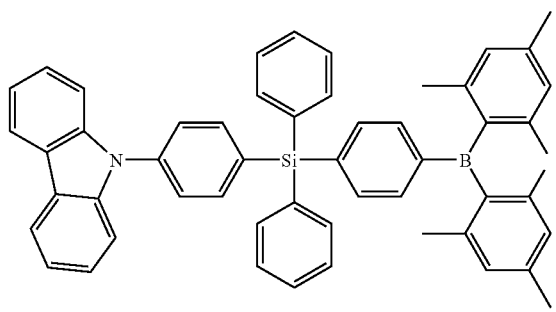

Carbazole (11.0 mmole, 0.1672 g) and the starting substance {4-[(4-Bromo-phenyl)-diphenyl-silanyl]-phenyl}-bis-(2,4,6-trimethyl-phenyl)-borane (1.0 mmole, 0.664 g), and Pd(dba)$_2$ (0.02 mmole, 0.011 g) are taken and then placed in a high-pressure pipe. In a glove box, P(t-Bu)$_3$ [0.016 mmole, 0.032 g, 1 mL (10%, in Hexane)] and NaOtBu (1.5 mmole, 0.144 g) are added and 2 mL of xylene as a solvent is added. The pipe is then sealed in the glove box and is placed in a 120° C. silicone oil bath. The reaction is carried out for 24 hrs. After the reaction is finished, the temperature of the mixture solution is returned to room temperature. The solution is filtered by silica and tripoli and then washed by methylene chloride. The filtrate is collected and dried to obtained yellowish solids. The yellowish solids are washed by ether. White solids are collected, that is, the compound BSiCN. The product yield is 60%.

$^1$H NMR (400 MHz, CDCl$_3$): δ: 8.12 (d, J=7.6 Hz, 2H), 7.76 (d, J=8.0 Hz, 2H), 7.63-7.59 (m, 7H), 7.53-7.38 (m, 13H), 7.29-7.26 (m, 2H), 6.80 (s, 4H), 2.28 (s, 6H), 2.01 (s, 12H). $^{13}$C NMR (100 MHz, CDCl$_3$): δ: 147.29, 141.72, 140.75, 140.55, 139.02, 138.73, 138.09, 137.85, 136.37, 135.87, 135.11, 133.67, 133.34, 129.85, 128.18, 128.03, 126.14, 125.91, 123.48, 120.27, 120.04, 109.87, 23.43, 21.20. HRMS (EI$^+$): Calcd for (C$_{54}$H$_{48}$BNSi): 749.3649; found: (M$^+$) 749.3651.

Example 4

N-(4-{1-[4-(1,1-dimseityboryl)phenyl]-1,1-diphenylsilyl}phenyl)-N,N-diphenylamine (hereinafter abbreviated as BSiPN)

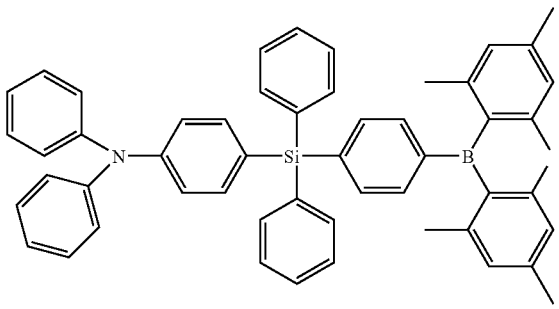

The synthetic method of BSiPN is the same as that in Example 3 except that diphenylamine is used instead of carbazole. The BSiPN product yield is 70%.

$^1$H NMR (400 MHz, CDCl$_3$): δ: 7.59-7.56 (m, 6H), 7.48 (d, J=8.0 Hz, 2H), 7.43-7.34 (m, 8H), 7.28-7.24 (m, 4H), 7.15-7.12 (m, 4H), 7.05-7.02 (m, 4H), 6.81 (s, 4H), 2.30 (s, 6H), 2.02 (s, 12H). $^{13}$C NMR (100 MHz, CDCl$_3$): δ: 149.10, 147.36, 141.80, 140.78, 138.96, 138.66, 137.27, 136.34, 135.85, 134.97, 134.45, 129.53, 129.30, 128.15, 127.82, 125.81, 125.09, 123.37, 121.67, 23.42, 21.20. HRMS (EI$^+$) Calcd for (C$_{54}$H$_{50}$BNSi): 751.3806; found: (M$^+$) 751.3807.

Example 5

The major physical properties of the compounds containing heteroatom-centered arylsilane derivatives disclosed in Example 1~Example 4 are measured and shown in Table 1.

TABLE 1

|  | BSi | BSiB | BSiCN | BSiPN |
|---|---|---|---|---|
| $\lambda^a_{abs}$ (nm) | 311, 269, 227 | 313, 270, 228 | 294, 266, 228 | 310, 270, 227 |
| $\lambda^b_{max}$ (nm) | 380 | 380 | 394 | 426 |
| $\lambda^c_{max}$ (nm) | 398 | 402 | 404 | 390, 516 |
| triplet state energy$^d$ (eV) | 2.95 | 2.95 | 2.95 | 2.92 |
| HOMO$^e$ (eV) | 6.29 (6.01) | 6.27 (6.05) | 5.92 (5.77) | 5.59 (5.40) |
| LUMO (eV) | 2.77 (2.49) | 2.75 (2.53) | 2.38 (2.23) | 2.20 (2.01) |
| Tm$^f$ (° C.) | 191.0 | 274.7 | 236.6 | — |
| Tg$^g$ (° C.) | 77.4 | 117.3 | 113.1 | 101.8 |
| Tc$^h$ (° C.) | 146.6 | 241.0 | 163.6 | — |

$^a$UV-vis absorption is measured by using CH$_2$Cl$_2$ as the solvent and having solution concentration of about 1 × 10$^{-5}$ M;
$^b$Photoluminescence of powder;
$^c$Photoluminescence is measured by using CH$_2$Cl$_2$ as the solvent and having solution concentration of about 1 × 10$^{-5}$ M;
$^d$EtOH is used as the solvent and the measurement is carried out at 77 K;
$^e$Redox measurement is carried out in CH$_2$Cl$_2$ with solution concentration of about 1 × 10$^{-3}$ M and the reported value is the value corresponding to Cp$_2$Fe/Cp$_2$Fe$^+$;
$^f$Melting point
$^g$Glass transition temperature
$^h$Crystal-growth temperature According to this embodiment, the compound containing heteroatom-centered arylsilane derivatives has excellent heat stability and high triplet-state energy difference. Therefore, as the compound containing heteroatom-centered arylsilane derivatives is applied in an organic electronic device, the excellent heat stability makes the lifetime of the organic electronic device increased. In addition, as the compound containing heteroatom-centered arylsilane derivatives is applied in an organic electroluminescence device, the compound containing heteroatom-centered arylsilane derivatives has high triplet-state energy difference, which can not be provided by the common blue phosphorescence host materials, and can be used together with various common phosphorescent materials, such as blue, green, and red phosphorescent materials, like iridium (Ir), platinum (Pt), and osmium (Os) metal complexes. Furthermore, by doped with various common phosphorescent materials, such as blue, green, and red phosphorescent materials, like iridium (Ir), platinum (Pt), and osmium (Os) metal complexes, the wavelength irradiated from the light-emitting layer can be adjusted according to actual needs.

In this embodiment, the compound containing heteroatom-centered arylsilane derivatives can be applied in an organic electroluminescence and/or phosphorescence device, especially used as a host material, an electron transport material, or a hole transport material. The compound containing heteroatom-centered arylsilane derivatives can also be applied as an electron transport material and a hole transport material in other organic electronic device. The organic electronic device can be a solar cell, an organic thin film transistor, an organic photoconductor, or other organic semiconducting device well-known to those who are skilled in the art.

In a second embodiment of the invention, an organic light emitting device is disclosed. Generally, the color of light emitted by the organic light emitting device is determined by the fluorescent organic material in the device. Therefore, by doping small amount of guest emitters with high luminance efficiency in host emitters, the recombination efficiency of carriers can be increased. These guest emitters have smaller energy gap, higher luminance efficiency and shorter recombination lifetime than the host emitters. Therefore, the excitons of the host emitters quickly transfer to the guest emitters through energy transition to carry out recombination effectively. Besides increasing luminance efficiency, the color of the emitted light covers the whole visible light region.

Generally, guest emitters are used together with host emitters by co-evaporation or dispersion, or by spin coating. Guest emitters receive energy from the excited host emitters through energy transfer or carrier trap to produce different colors, such as red, green, and blue, and to increase luminance efficiency. Besides the above mentioned fluorescence guest emitters, new development in phosphorescence material is also researched. As an organic molecule is excited, one quarter of excited electrons form asymmetric spin siglet state and release energy through fluorescence. However, three quarters of excited electrons form symmetric spin triplet state but do not release energy through radiated phosphorescence to thereby lose efficiency. At present, the material capable of releasing the triplet-state energy of the excited electrons through radiated phosphorescence usually is an organic metallic compound having a center transition metal, such as osmium (Os), iridium (Ir), platinum (Pt), europium (Eu), ruthenium (Ru), etc., and a nitrogen-containing heterocyclic compound as its ligand.

According to this embodiment, the organic light emitting device comprises a pair of electrodes and at least one organic layer provided between the electrodes. The at least one organic layer comprises one light-emitting layer and at least one of the organic layers comprises one compound containing heteroatom-centered arylsilane derivatives, having the following general structure:

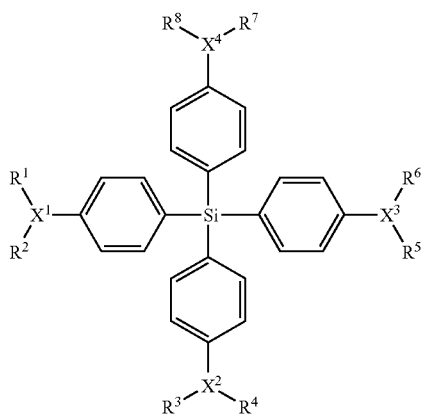

where $X^1$, $X^2$, $X^3$, and $X^4$ can be identical or different and $X^1$, $X^2$, $X^3$, and $X^4$ are independently selected from the group consisting of the following: H, B, N, P=O, Si—$R^9$; and $R^1$, $R^2$, $R^3$, $R^4$, $R^5$, $R^6$, $R^7$, $R^8$, and $R^9$ can be identical or different and $R^1$, $R^2$, $R^3$, $R^4$, $R^5$, $R^6$, $R^7$, $R^8$, and $R^9$ are independently selected from aryl group or heterocyclic aryl group containing one or more substituents. It is noted that at least one of the $X^1$, $X^2$, $X^3$, and $X^4$ is not H. When $X^1$ is H, $R^1$ and $R^2$ do not exist in the structure. When $X^2$ is H, $R^3$ and $R^4$ do not exist in the structure. When $X^3$ is H, $R^5$ and $R^6$ do not exist in the structure. As $X^4$ is H, $R^7$ and $R^8$ do not exist in the structure.

The aryl group comprises phenyl, naphthyl, diphenyl, anthryl, pyrenyl, phenanthryl, fluorene, or other multi-phenyl group.

The heterocyclic aryl group comprises pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, phenanthroline, or other heterocyclic aryl group.

In addition, $R^1$, $R^2$, $R^3$, $R^4$, $R^5$, $R^6$, $R^7$, $R^8$, and $R^9$ groups each can have one or more substituents. The substituent is independently selected from the group consisting of the following: H atom, halogen atom (such as fluorine, chlorine, bromine, iodine), aryl group, halogen substituted aryl group, C1-C20 haloalkyl substituted aryl group, C1-C20 haloalkyl substituted aralkyl group, C1-C20 alkyl group with aryl substituent, C1-C20 alkyl group (such as methyl, ethyl, butyl, cyclohexyl), C1-C20 alkoxy group, amino group, C1-C20 substituted amino group, nitrile group, nitro group, carbonyl group, cyano group (—CN), and heterocyclic group.

In a preferred example of this embodiment, the compound containing heteroatom-centered arylsilane derivatives is applied in the light-emitting layer of the organic light emitting device. According to another preferred example of this embodiment, the compound containing heteroatom-centered arylsilane derivatives is applied as a host material in the light-emitting layer of the organic light emitting device. The light-emitting layer can further comprise a guest emitting material and the guest emitting material comprises a transition metal complex. The transition metal of the transition metal complex can be selected from the group consisting of the following: Ir, Pt, Os, Eu, and Ru. The guest emitting material can be a blue, green, or red phosphorescence material. According to another preferred example of this embodiment, the compound containing heteroatom-centered arylsilane derivatives can be applied in an electron transport layer of the organic light emitting device.

General Process for Fabricating an Organic Light Emitting Device

An ITO glass with etched circuitry is placed in a cleaning liquid (neutral cleanser:deionized water=1:50) and carried out supersonic oscillation for 5 minutes. Then, the ITO glass is brushed by a soft brush and sequentially carried out the following steps: placing in 50 mL of deionized water, oscillating in electronic grade acetone for 5 minutes, and drying by nitrogen. The cleaned ITO glass is placed in an ultraviolet-ozone machine for 5 minutes. Finally, the ITO glass with the ITO surface facing downward is provided on the substrate holder in an evaporator. The chamber is vacuumed. The process of evaporating thin film does not start until the pressure in the chamber reaches $5\times10^{-6}$ torr. The conditions of evaporation are as follows. The evaporation rate for the organic films is controlled at 1~2 Å/s and then the expected organic films are evaporated sequentially. The evaporation rate of magnesium for the metal film is 5 Å/s while that of silver is 0.5 Å/s (Mg:Ag=10:1). The Mg—Ag co-evaporated metal film has a thickness of 55 nm. Finally, a silver layer having a thickness of 100 nm as a protection layer is formed. In the case of choosing LiF/Al system as metal, firstly LiF is evaporated with a rate of 0.1 Å/s to form a film with a thickness of 1 nm and secondly an aluminum layer having a thickness of 100 nm as a protection layer is formed. During the process of evaporation, the rotational speed of the device is about 20 rpm. After the evaporation process is finished, the metal electrode is stayed for 20 minutes to cool and then the chamber is filled with nitrogen until the pressure returns normal pressure.

On the other hand, after the OLED device is fabricated, the EL spectrum and CIE coordination of the device are measured by F-4500 Hitachi. In addition, the properties, such as current, voltage, and brightness of the device are measured by Kiethley 2400 programmable voltage-current source. The measurements are carried out at room temperature (about 25° C.) and 1 atm.

Example 6

By the general process of fabricating OLED, BSi is the host emitting material and five OLEDs are fabricated by using blue phosphorescence materials as dopants. The doped blue phosphorescence materials have the following structures and the structure of each device is shown in the following.

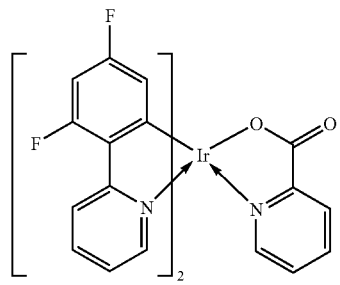

FIrpic

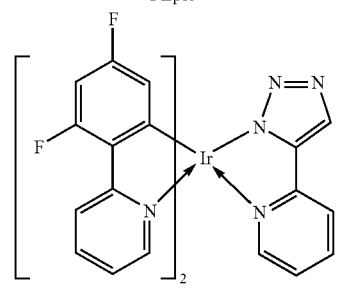

(dfppy)$_2$Irpytz

Device 2A: NPB(40 nm)/mcp(10 nm)/BSi: (dfppy)$_2$Ir(pytz) (6%)(30 nm)/BCP(15 nm)/Alq(30 nm)
Device 2B: NPB(30 nm)/mcp(20 nm)/BSi: (dfppy)$_2$Ir(pytz) (5.6%)(30 nm)/TPBI(20 nm)
Device 2C: NPB(40 nm)/mcp(20 nm)/BSi: (dfppy)$_2$Ir(pytz) (5%)(30 nm)
Device 2D: NPB(40 nm)/mcp(10 nm)/BSi:(dfppy)$_2$Ir(pytz) (6%)(30 nm)/BCP(15 nm)/sean105(30 nm)
Device 2E: 2-TNATA(10 nm)/NPB(20 nm)/mcp(20 nm)/ BSi:FIrpic(7.0%)(30 nm)/TPBI(20 nm)

The cathode of the devices 2A~2E is Mg:Ag(55 nm)/Ag (100 nm). The optical properties and efficiency of the devices 2A~2E are measured and shown in Table 2.

TABLE 2

| device (%) | $V_d^a$ (V) | Lum$^b$ (cd/m$^2$) | $\eta_{ext}^c$ (%) | $\eta_c^d$ cd/A | $\eta_p^e$ (lm/W) | C.I.E |
|---|---|---|---|---|---|---|
| 2A | 5.7 | 2514 | 7.9@10.0 V | 14.4@10.0 V | 4.7@9.5 V | 0.13, 0.26@8 v |
| 2B | 5.8 | 1868 | 6.0@9.5 V | 9.2@9.5 V | 3.0@9.5 V | 0.13, 0.20@8 v |
| 2C | 5.4 | 970 | 3.7@8.0 V | 5.1@8.0 V | 2.0@8.0 V | 0.13, 0.17@8 v |
| 2D | 6.2 | 1081 | 6.0@9.0 V | 10.0@9.0 V | 3.6@9.0 V | 0.14, 0.22@8 v |
| 2E | 6.2 | 3265 | 9.6@11.5 V | 18.9@11.5 V | 5.2@11.0 V | 0.14, 0.29@8 v |

$^a$Drive voltage ($V_d$);
$^b$maximum luminescence (L);
$^c$maximum external quantum efficiency ($\eta_{ext}$);
$^d$maximum current efficiency ($\eta_c$);
$^e$maximum power efficiency ($\eta_p$).

Example 7

By the general process of fabricating OLED, BSiB is the host emitting material and three OLEDs are fabricated by using blue phosphorescence materials as dopants. The doped blue phosphorescence materials have the following structures and the structure of each device is shown in the following.

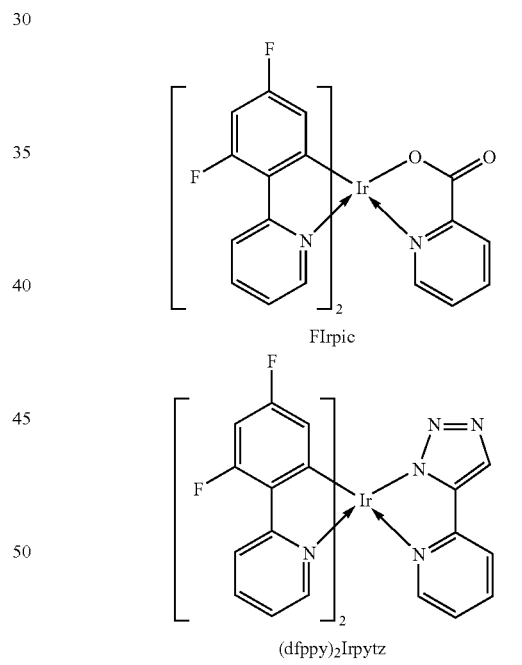

Device 2F: NPB(30 nm)/mcp(20 nm)/BSiB: (dfppy)$_2$Ir(pytz) (5%)(30 nm)/BCP(15 nm)/Alq(30 nm)
Device 2G: 2-TNATA(10 nm)/NPB(20 nm)/mcp(20 nm)/ BSiB: (dfppy)$_2$Ir(pytz) (7%)(30 nm)/TPBI(20 nm)
Device 2H: 2-TNATA(10 nm)/NPB(20 nm)/mcp(20 nm)/ BSiB:FIrpic(7%)(30 nm)/TPBI(20 nm)

The cathode of the devices 2F~2H is Mg:Ag(55 nm)/Ag (100 nm). The optical properties and efficiency of the devices 2F~2H are measured and shown in Table 3.

TABLE 3

| device | $V_d{}^a$ (V) | Lum$^b$ (cd/m²) | $\eta_{ext}{}^c$ (%) | $\eta_c{}^d$ cd/A | $\eta_p{}^e$ (lm/W) | C.I.E |
|---|---|---|---|---|---|---|
| 2F | 6.0 | 2062 | 8.2@11.0 V | 15.3@11.0 V | 4.5@10.5 V | 0.14, 0.29@8 v |
| 2G | 5.7 | 2006 | 8.2@9.5 V | 13.0@9.5 V | 4.5@9.0 V | 0.13, 0.21@8 v |
| 2H | 5.5 | 2850 | 8.7@9.5 V | 18.1@9.5 V | 6.0@9.5 V | 0.14, 0.32@8 v |

$^a$Drive voltage ($V_d$);
$^b$maximum luminescence (L);
$^c$maximum external quantum efficiency ($\eta_{ext}$);
$^d$maximum current efficiency ($\eta_c$);
$^e$maximum power efficiency ($\eta_p$).

Example 8

By the general process of fabricating OLED, BSiCN and FIrpic are used to form three OLEDs. The doped blue phosphorescence material has the following structure and the structure of each device is shown in the following.

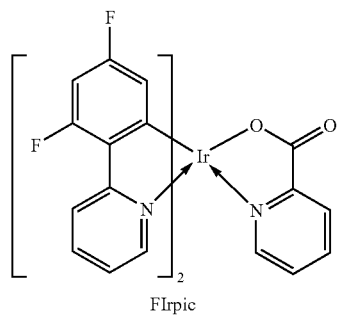

FIrpic

Device 2I: NPB(30 nm)/mcp(20 nm)/BSiCN:FIrpic(7%)(30 nm)/BCP(15 nm)/Alq(30 nm)
Device 2J: TCTA(30 nm)/mcp(20 nm)/BSiCN:FIrpic(7%)(30 nm)/BCP(15 nm)/Alq(30 nm)
Device 2K: NPB(30 nm)/mcp(20 nm)/BSiCN:FIrpic(7%)(30 nm)/TPBI(20 nm)

The cathode of the devices 2I~2K is Mg:Ag(55 nm)/Ag (100 nm). The optical properties and efficiency of the devices 2I~2K are measured and shown in Table 4.

Example 9

By the general process of fabricating OLED, BSiCN and (dfppy)₂Irpytz are used to form two OLEDs. The doped blue phosphorescence material has the following structure and the structure of each device is shown in the following.

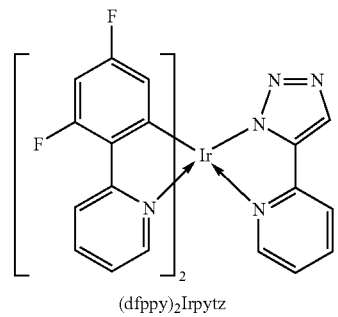

(dfppy)₂Irpytz

Device 2L: NPB(30 nm)/mcp(20 nm)/BSiCN:(dfppypytz)₂Irpytz (7.3%)(30 nm)/TPBI(20 nm)
Device 2M: 2-TNATA(10 nm)/NPB (20 nm)/mcp(20 nm)/BSiCN:(dfppypytz)₂Irpytz (7%)(30 nm)/TPBI(20 nm)

The cathode of the devices 2L~2M is Mg:Ag(55 nm)/Ag (100 nm). The optical properties and efficiency of the devices 2L~2M are measured and shown in Table 5.

TABLE 4

| device | $V_d{}^a$ (V) | Lum$^b$ (cd/m²) | $\eta_{ext}{}^c$ (%) | $\eta_c{}^d$ cd/A | $\eta_p{}^e$ (lm/W) | C.I.E |
|---|---|---|---|---|---|---|
| 2I | 4.6 | 2776 | 5.5@10.0 V | 13.6@10.0 V | 4.5@9.5 V | 0.18, 0.41@8 v |
| 2J | 5.0 | 2717 | 6.6@11.5 V | 15.6@11.5 V | 4.3@11.5 V | 0.17, 0.40@8 v |
| 2K | 4.5 | 2750 | 5.5@8.0 V | 11.7@8.0 V | 4.8@7.5 V | 0.15, 0.33@8 v |

$^a$Drive voltage ($V_d$),
$^b$maximum luminescence (L),
$^c$maximum external quantum efficiency ($\eta_{ext}$),
$^d$maximum current efficiency ($\eta_c$),
$^e$maximum power efficiency ($\eta_p$)

TABLE 5

| device (%) | $V_d^a$ (V) | Lum$^b$ (cd/m$^2$) | $\eta_{ex}^c$ (%) | $\eta_c^d$ cd/A | $\eta_p^e$ (lm/W) | C.I.E |
|---|---|---|---|---|---|---|
| 2L | 4.6 | 2140 | 6.4@7.0 V | 11.0@6.5 V | 5.0@6.5 V | 0.15, 0.23@8 v |
| 2M | 4.5 | 1950 | 6.8@8.0 V | 10.7@8.0 V | 4.2@8.0 V | 0.13, 0.21@8 v |

$^a$Drive voltage (V$_d$);
$^b$maximum luminescence (L);
$^c$maximum external quantum efficiency ($\eta_{ext}$);
$^d$maximum current efficiency ($\eta_c$);
$^e$maximum power efficiency ($\eta_p$).

Example 10

By the general process of fabricating OLED, BSiPN is the host emitting material and two OLEDs are fabricated by using blue phosphorescence materials as dopants. The doped blue phosphorescence materials have the following structures and the structure of each device is shown in the following.

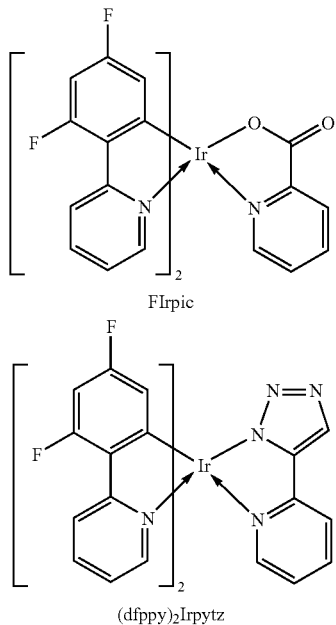

FIrpic (dfppy)$_2$Irpytz

Device 2N: 2-TNATA(10 nm)/NPB(30 nm)/mcp(20 nm)/ BSiPN:FIrpic(7%)(30 nm)/TPBI(20 nm)
Device 2O: 2-TNATA(10 nm)/NPB(20 nm)/mcp(20 nm)/ BSiPN:(dfppypytz)$_2$Irpytz (7%)(30 nm)/TPBI(20 nm)

The cathode of the devices 2N~2O is Mg:Ag(55 nm)/Ag (100 nm). The optical properties and efficiency of the devices 2N~2O are measured and shown in Table 6.

TABLE 6

| device (%) | $V_d^a$ (V) | Lum$^b$ (cd/m$^2$) | $\eta_{ext}^c$ (%) | $\eta_c^d$ cd/A | $\eta_p^e$ (lm/W) | C.I.E |
|---|---|---|---|---|---|---|
| 2N | 5.7 | 2624 | 6.9@10.0 V | 14.0@10.0 V | 4.5@9.5 V | 0.13, 0.31@8 v |
| 2O | 5.0 | 1460 | 5.8@7.0 V | 8.7@7.0 V | 4.0@7.0 V | 0.13, 0.20@8 v |

$^a$Drive voltage (V$_d$);
$^b$maximum luminescence (L);
$^c$maximum external quantum efficiency ($\eta_{ext}$);
$^d$maximum current efficiency ($\eta_c$);
$^e$maximum power efficiency ($\eta_p$).

In this embodiment, the compound containing heteroatom-centered arylsilane derivatives is applied as a host material, an electron transport material, or a hole transport material in an organic electroluminescence device.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A compound of heteroatom-centered arylsilane derivatives, comprising the following general structure:

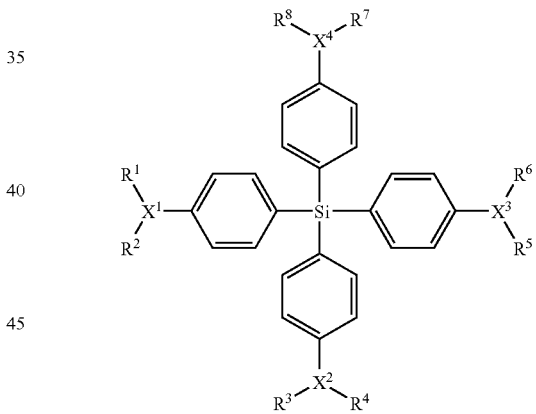

where $X^1$, $X^2$, $X^3$, and $X^4$ can be identical or different and $X^1$, $X^2$, $X^3$, and $X^4$ are independently selected from the group consisting of the following: H, B, N, P=O, Si—$R^9$; and $R^1$, $R^2$, $R^3$, $R^4$, $R^5$, $R^6$, $R^7$, $R^8$, and $R^9$ can be identical or different and $R^1$, $R^2$, $R^3$, $R^4$, $R^5$, $R^6$, $R^7$, $R^8$, and $R^9$ are independently selected from aryl group or heterocyclic aryl group of one or more substituents;

wherein at least one of the $X^1$, $X^2$, $X^3$, and $X^4$ is not H,
wherein $X^1$ and $X^3$ are not N simultaneously,
wherein when $X^1$ is B and $X^3$ is N, $R^5$ and $R^6$ are not as naphthyl group.

2. The compound according to claim 1, wherein said aryl group comprises one functional group selected from the group consisting of the following: phenyl, naphthyl, diphenyl, anthryl, pyrenyl, phenanthryl, fluorene, or other multiphenyl group.

3. The compound according to claim 1, wherein said heterocyclic aryl group comprises one functional group selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, phenanthroline, or other heterocyclic aryl group.

4. The compound according to claim 1, wherein said $R^1$, $R^2$, $R^3$, $R^4$, $R^5$, $R^6$, $R^7$, $R^8$, and $R^9$ groups each has one or more substituents and said substituent is independently selected from the group consisting of the following: H atom, halogen atom, aryl group, halogen substituted aryl group, C1-C20 haloalkyl substituted aryl group, C1-C20 haloalkyl substituted aralkyl group, aryl substituted C1-C20 alkyl group, C1-C20 alkyl group, C1-C20 alkoxy group, amino group, C1-C20 substituted amino group, nitrile group, nitro group, carbonyl group, cyano group (—CN), and heterocyclic group.

5. The compound according to claim 1, wherein the compound is utilized in an organic electroluminescence and/or phosphorescence device.

6. The compound according to claim 1, wherein the compound is utilized as a host material in an organic electroluminescence and/or phosphorescence device.

7. The compound according to claim 1, wherein the compound is utilized as an electron transport material in an organic electronic device.

8. The compound according to claim 1, wherein the compound is utilized as a hole transport material in an organic electronic device.

* * * * *